United States Patent [19]

Outtrup et al.

[11] Patent Number: 5,468,416
[45] Date of Patent: Nov. 21, 1995

[54] DETERGENT ENZYMES

[75] Inventors: Helle Outtrup, Ballerup; Dorrit A. Aaslyng, Roskilde; Claus Dambmann, Soeborg; Shamkant A. Patkar, Lyngby, all of Denmark

[73] Assignee: Novo Nordisk A/S, Bagsvaerd, Denmark

[21] Appl. No.: 193,112

[22] PCT Filed: Sep. 11, 1992

[86] PCT No.: PCT/DK92/00273

§ 371 Date: Feb. 8, 1994

§ 102(e) Date: Feb. 8, 1994

[87] PCT Pub. No.: WO93/05134

PCT Pub. Date: Mar. 18, 1993

[51] Int. Cl.⁶ ................................................ C11D 3/386
[52] U.S. Cl. ............................. 252/174.12; 252/DIG. 16; 455/223; 455/224; 455/225
[58] Field of Search ........................... 435/223–225, 435/174.12, DIG. 12

[56] References Cited

U.S. PATENT DOCUMENTS 5,273,896 12/1993 Pedersen et al. ........................ 435/192

FOREIGN PATENT DOCUMENTS 0335023 10/1989 European Pat. Off. .
9101642 2/1991 WIPO .

Primary Examiner—Paul Lieberman
Assistant Examiner—Kery Fairs
Attorney, Agent, or Firm—Steve T. Zelson; Elias J. Lambiris

[57] ABSTRACT

This inventions is in the field of detergent enzymes. More specifically, the invention relates to the use of proteases from fungi of the genus Verticillium for detergent purposes.

8 Claims, 2 Drawing Sheets

DETERGENT ENZYMES

CROSS-REFERENCE TO RELATED APPLICATION

This application is a continuation of PCT/DK92/00273 filed Sep. 11, 1992, which is incorporated herein by reference.

TECHNICAL FIELD

This invention is in the field of detergent enzymes. More specifically, the invention relates to the use of proteases derived from fungi of the genus Verticillium for detergent purposes.

1. Background Art

Fungi belonging to the genus Verticillium are well known in the literature, and they are known to be pathogenic to insects and plants. The fungi are also known to produce proteolytic enzymes which have been investigated in relation to the pathogenicity of the fungi.

2. Summary of the Invention

It has now surprisingly been found that proteases derived from members of the fungi Verticillium posses excellent washing performance.

Accordingly, the present invention provides detergent compositions comprising proteases obtainable from, or proteases having immunochemical properties identical or partially identical to those of a protease derived from any of the strains CBS No. 145.70; CBS No. 146.70; CBS No. 247.68; and CBS No. 464.88.

In another aspect, the invention provides detergent compositions comprising proteases obtainable from a member of the genus Verticillium, or a mutant or a variant thereof.

In yet another aspect, the invention provides detergent additives comprising proteases obtainable from, or proteases having immunochemical properties identical or partially identical to those of a protease derived from any of the strains CBS No. 145.70; CBS No. 146.70; CBS No. 247.68; and CBS No. 464.88.

In a further aspect, the invention provides detergent additives comprising proteases obtainable from a member of the genus Verticillium, or a mutant or a variant thereof.

BRIEF DESCRIPTION OF DRAWINGS

The present invention is further illustrated by reference to the accompanying drawings, in which.

DETAILED DISCLOSURE OF THE INVENTION

Figure 1:
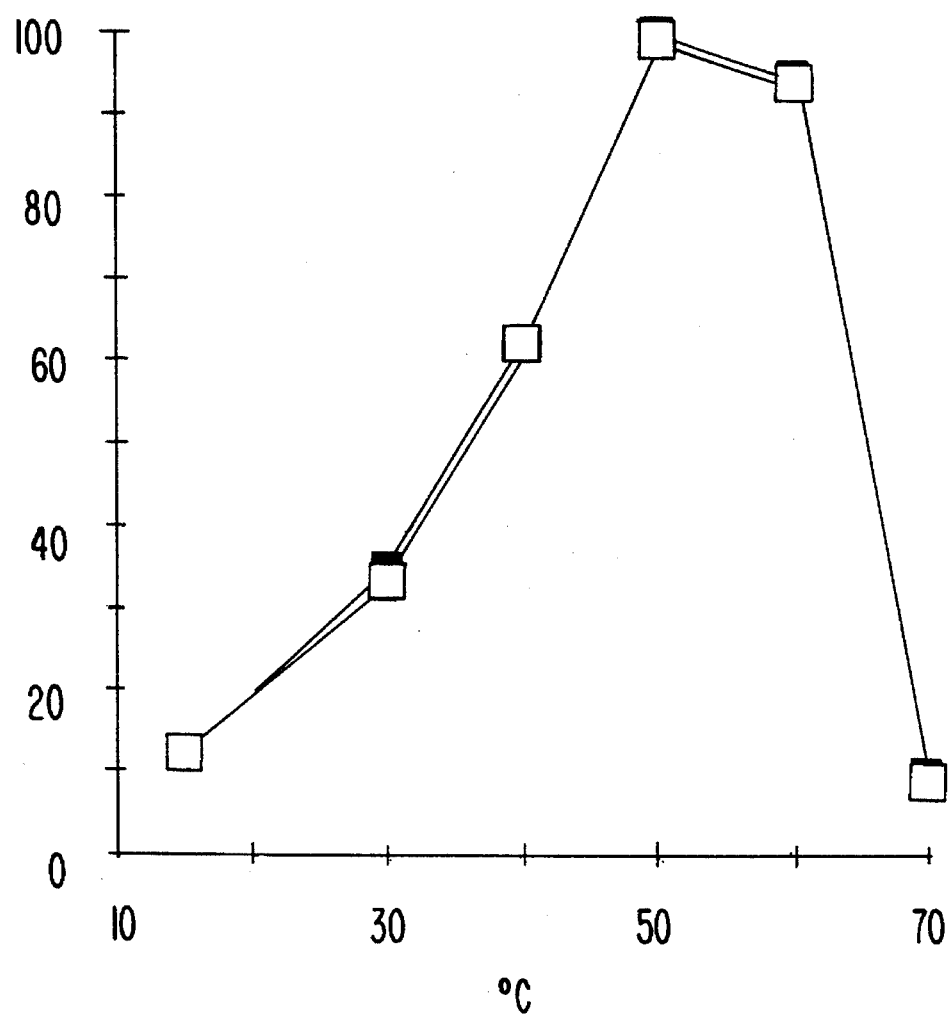
FIG. 1 shows the relation between temperature (°C.) and proteolytic activity (% relative) of an enzyme of the invention (■ at pH 9.5; □ at pH 9.5 with 0.1% STPP added)

The present invention provides detergent compositions comprising proteases obtainable from a fungal strain of the genus Verticillium. Fungi belonging to the genus Verticillium are well known and described in the literature. Strains of Verticillium have been deposited and made available from various international depositary institutes, e.g. CBS No. 247.68; CBS No. 145.70; CBS No. 146.70; or CBS No. 464.88.

The proteases are obtainable by methods known and described in the literature, e.g. by cultivation of a protease producing strain of the genus Verticillium in a suitable nutrient medium, containing carbon and nitrogen sources and inorganic salts, followed by recovery of the desired enzyme, or may e.g. be produced by employing recombinant DNA technology.

The Proteases

In the context of this invention, suitable proteases are the proteases obtainable from strains of Verticillium, or routants or variants thereof or proteases having immunochemical properties identical or partially identical to a protease obtainable from a strain of Verticillium, e.g. *V. bulbillosum*.

By an enzyme variant or mutated enzyme is meant an enzyme obtainable by alteration of the DNA nucleotide sequence of the parent gene or its derivatives. The enzyme variant or mutated enzyme may be expressed and produced when the DNA nucleotide sequence encoding the enzyme is inserted into a suitable vector in a suitable host organism. The host organism is not necessarily identical to the organism from which the parent gene originated.

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Detergent Compositions

The detergent composition of the invention may comprise one or more surfactants, which may be of an anionic, non-ionic, cat-ionic, amphoteric or zwitterionic type, or a mixture of these. Typical examples of anionic surfactants are linear alkyl benzene sulfonates (LAS); alkyl sulfates (AS); alpha olefin sulfonates (AOS); alcohol ethoxy sulfates (AES) and alkali metal salts of natural fatty acids. Examples of non-ionic surfactants are alkyl polyethylene glycol ethers; nonylphenol polyethylene glycol ethers; fatty acids esters of sucrose and glucose; and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The so detergent composition of the invention may be formulated substantially as described in J. Falbe [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes. e.g. lipases;

amylases; celluloses; oxidases; and/or peroxidases, conventionally included in detergent compositions, as well as proteases of other origin.

The protease of the invention may be included in a detergent composition by adding separate additives containing the detergent protease, or by adding a combined additive comprising different detergent enzymes.

The additive of the invention, i.e. a separated additive or a combined additive, can be formulated e.g. as granulates, liquids, slurries, etc. Preferred detergent additive formulations are non-dusting granulates, liquids, in particular stabilized liquids, slurries, or protected enzymes. Dust free granulates may be produced according to e.g. GB Patent No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol; a sugar or sugar alcohol; lactic acid or boric acid, according to established methods. Other enzyme stabilizers are well known in the art. Protected enzymes may be prepared according to the method disclosed in EP Patent Application No. 238,216.

The invention is further illustrated in the following examples which are not intended to be in any way limiting to the scope of the invention as claimed.

EXAMPLE 1

Preparation Example

The strain *Verticillium bulbillosum,* CBS 247.68, was cultivated at 25° C. on a rotary shaking table (240 r.p.m.) in 500 ml baffled Erlenmeyer flasks containing 100 ml of medium of the following composition (per liter):

| | |
|---|---|
| Sucrose | 100 g |
| Soybean flour | 40 g |
| Na$_2$HPO$_4$ × 12 H$_2$O | 10 g |
| Pluronic ® | 0.1 g |

The medium is sterilized by heating at 120° C. for 45 minutes.

After 12 days of incubation a proteolytic activity of the culture of 21 CPU/l was determined using the method described below.

After separation of the solid material the protease was purified by a conventional chromatographic method.

Yield from 1 l of culture broth was 30 ml with 270 CPU/l. Purity was more than 90% as judged by SDS-PAGE.

Preparations from the strains *V. bulbillosum,* CBS 145.70; *V. bulbillosum,* CBS 146.70; and *V. suchlasporium var. suchlasporium,* CBS 464.88, were obtained in similar ways.

EXAMPLE 2

Characterization of the Enzyme

The preparation prepared in accordance with Example 1 was subjected to the following characterization.

A molecular weight of 30 kD was determined by SDS-PAGE. A pI higher than 9.3 was determined by isoelectric focusing on LKB Ampholine® PAG plates. The protease activity is inhibited by PMSF, α-1-antitrypsin and Turkey-egg-white proteinase inhibitor. EDTA and soybean-protein inhibitor do not influence the protease activity.

The temperature activity relationship was determined with casein as substrate. The assay for proteolytic activity described previously was used with the modification that the incubation temperature was varied in the interval of from 15° to 70° C. The result is shown in FIG. 1. The enzyme possesses proteolytic activity from temperatures below 15° C. to above 70° C., and a temperature optimum within the range of 45° to 65° C.; around 55° C.

Figure 2:
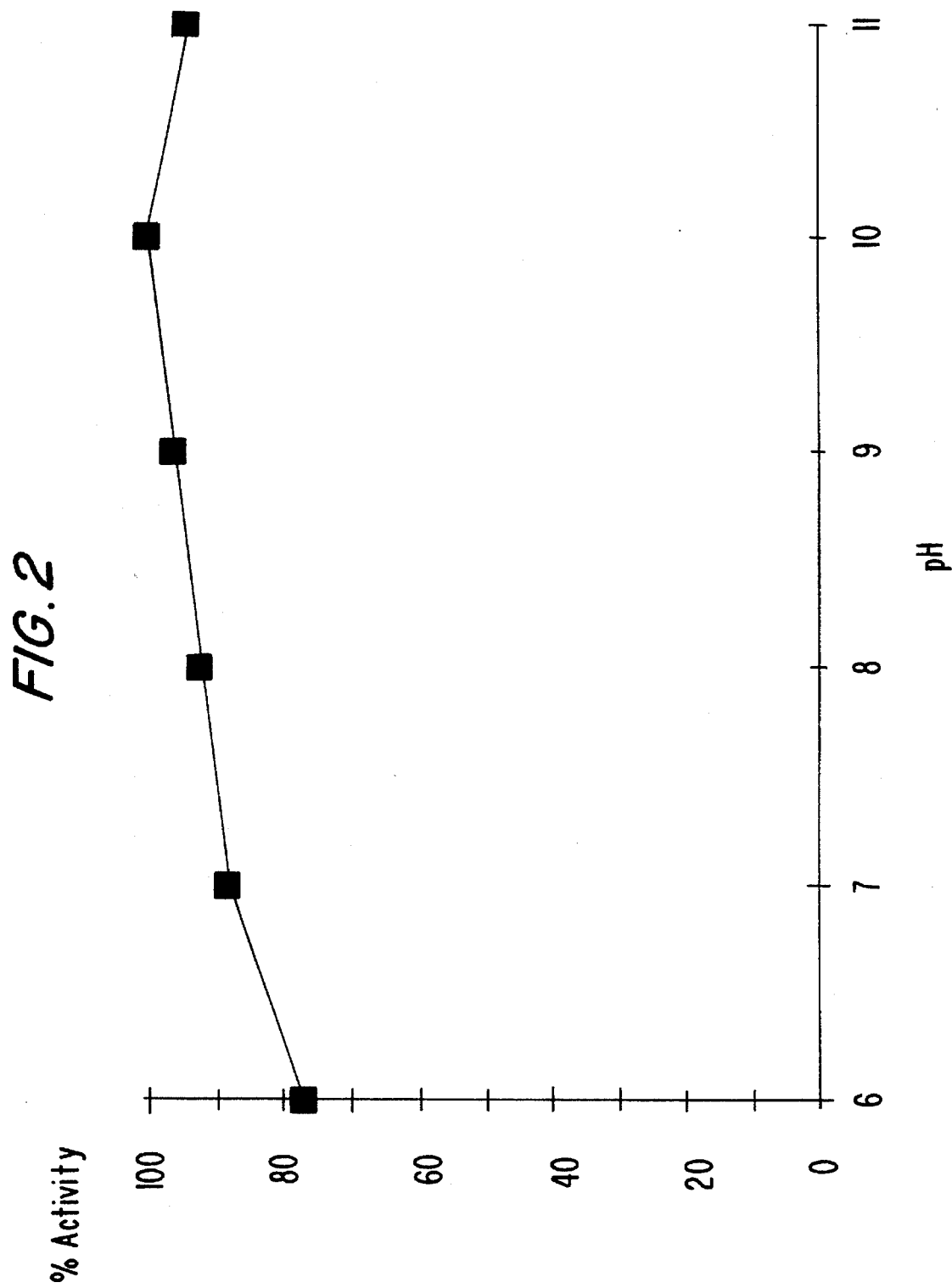
FIG. 2 shows the relation between pH and proteolytic activity (% relative) of an enzyme of the invention.

The dependence of activity on pH was determined by the same procedure, using buffers adjusted to predetermined pH values in the pH range of from 6 to 11. The result is shown in FIG. 2. The enzyme possesses proteolytic activity at pH values below 6 to above 11, with a pH optimum in the range of pH 8 to pH 11.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228, describing the analytical method, is available upon request to Novo Nordisk A/S, Denmark, which folder is hereby included by reference.

EXAMPLE 3

Wash Performance

Two sets of wash performance tests were accomplished on grass juice soiled cotton at 20° C., isothermally for 10 minutes.

In the first set 2.0 g/l of a commercial American type powder detergent were used. The detergent was dissolved in approx. 6° dH (German Hardness) water. The pH was 9.5. The results of these tests are shown in Table 1.

In the second set 2.0 g/l of a commercial American type powder detergent with bleach and activator were used. The detergent was dissolved in approx. 6° dH (German Hardness) water. The pH was 9.5. The results of these tests are shown in Table 2.

In both sets the textile/wash liquor ratio was 6 g of textile per liter of wash liquor.

Subsequent to washing, the cloths were rinsed in running tap-water and air-dried. The remission (% R) was determined at 460 nm.

As a measure of the wash performance differential remission, ΔR, was used being equal to the remission after wash with enzyme added, minus the remission after wash with no enzyme added.

TABLE 1

The differential remission, Δ R, measured after wash in a commercial American type powder detergent.

| Strain No. | Enzyme dosage (CPU/l) | | | |
|---|---|---|---|---|
| (CBS) | 0.01 | 0.05 | 0.1 | 0.5 |
| 145.70 | 11 | 17.8 | 18.9 | 19.3 |
| 247.68 | 7.6 | 16 | 19 | 19.7 |
| 464.88 | 8.1 | 15.2 | 19.3 | 19.9 |

TABLE 2

The differential remission, Δ R, measured
after wash in a commercial American type powder
detergent with bleach and activator.

| Strain No. | Enzyme dosage (CPU/l) | | | |
|---|---|---|---|---|
| (CBS) | 0.01 | 0.05 | 0.1 | 0.5 |
| 145.70 | 8.4 | 13.5 | 13.6 | 13.8 |
| 247.68 | 8.4 | 12.8 | 14.1 | 14.1 |
| 464.88 | 7.3 | 13.0 | 14.4 | 14.7 |

As indicated by the differential remission values the proteases of the invention are well suited for use as detergent enzymes.

We claim:

1. A detergent composition comprising a surfactant and a protease derived from a strain of the genus Verticillium selected from the group consisting of *Verticillium bulbillosum* CBS No. 145.70, *Verticillium bulbillosum CBS No. 146.70*, *Verticillium bulbillosum CBS No. 247.68*, and *Verticillium suchlasporium var. suchlasporium* CBS No. 464.88, wherein the protease has a pH optimum in the range of 8–11 and a temperature optimum in the range of 45°–65° C.

2. The detergent composition according to claim 1, wherein the protease has a temperature optimum of about 55° C.

3. The detergent composition according to claim 1, wherein the protease has a molecular weight of 30 kD.

4. The detergent composition according to claim 1, wherein the protease has an isoelectric point of greater than 9.3.

5. The detergent composition according to claim 1, wherein the protease is inhibited by PMSF, α-1-antitrypsin and Turkey egg white protease inhibitor.

6. The detergent composition according to claim 1, wherein the activity of the protease is not influenced by EDTA and soybean protein inhibitor.

7. The detergent composition according to claim 1, wherein the protease is derived from a strain of *Verticillium bulbillosum*.

8. A detergent composition according to claim 1, further comprising one or more other enzymes selected from the group consisting of amylases, lipases, cellulases, oxodases, and peroxidases.

* * * * *